United States Patent
Duda et al.

(10) Patent No.: US 8,343,153 B2
(45) Date of Patent: Jan. 1, 2013

(54) COMPONENT AND METHOD FOR ASSEMBLING AN IMPLANT ARRANGEMENT

(75) Inventors: Georg Duda, Berlin (DE); Markus Heller, Berlin (DE)

(73) Assignee: Synthes USA, LLC, West Chester, PA (US)

( * ) Notice: Subject to any disclaimer, the term of this patent is extended or adjusted under 35 U.S.C. 154(b) by 1223 days.

(21) Appl. No.: 10/597,842

(22) PCT Filed: Feb. 10, 2005

(86) PCT No.: PCT/DE2005/000233
§ 371 (c)(1),
(2), (4) Date: Oct. 12, 2007

(87) PCT Pub. No.: WO2005/074821
PCT Pub. Date: Aug. 18, 2005

(65) Prior Publication Data
US 2008/0154265 A1 Jun. 26, 2008

(30) Foreign Application Priority Data
Feb. 10, 2004 (DE) .......................... 10 2004 006 501

(51) Int. Cl.
*A61B 17/80* (2006.01)
*A61B 5/00* (2006.01)
*A61F 2/30* (2006.01)
*A61M 5/142* (2006.01)

(52) U.S. Cl. ..................... 606/70; 623/19.11; 604/891.1

(58) Field of Classification Search ................... 606/70, 606/280–321, 71, 74, 75, 92–94, 102; 623/16; 600/300, 431, 302; 604/891.1
See application file for complete search history.

(56) References Cited

U.S. PATENT DOCUMENTS

| 4,186,749 A | 2/1980 | Fryer |
| 5,725,578 A * | 3/1998 | Knapp et al. .................. 128/898 |
| 5,769,893 A | 6/1998 | Shah |

(Continued)

FOREIGN PATENT DOCUMENTS

DE 4132021 A1 4/1993

(Continued)

OTHER PUBLICATIONS

G.N. Dudas, et al, "Does Partial Weight Bearing Unload a Healing Bone in External Ring Fixation", Langbecks Arch Surg, Oct. 2003, pp. 298-304.

*Primary Examiner* — Kevin T Truong
*Assistant Examiner* — Christopher Beccia
(74) *Attorney, Agent, or Firm* — Fay Kaplun & Marcin, LLP

(57) ABSTRACT

The invention refers to a component for arrangement at an implant as well as a method for the assembling of an implant arrangement. The component comprises a basic component, at least one sensor arranged in the basic component for the detection of a measurement variable and for the generation of measuring data for the detected measurement variable, a telemetry device arranged in the basic component for transmitting and receiving data and a data transmission connection between the at least one sensor device and the telemetry device for the transmission of data between the at least one sensor device and the telemetry device, whereby the data comprise the measuring data. At the basic component, assembly means for mounting the basic component in an implant recess are formed.

16 Claims, 5 Drawing Sheets

U.S. PATENT DOCUMENTS

Figure 1:
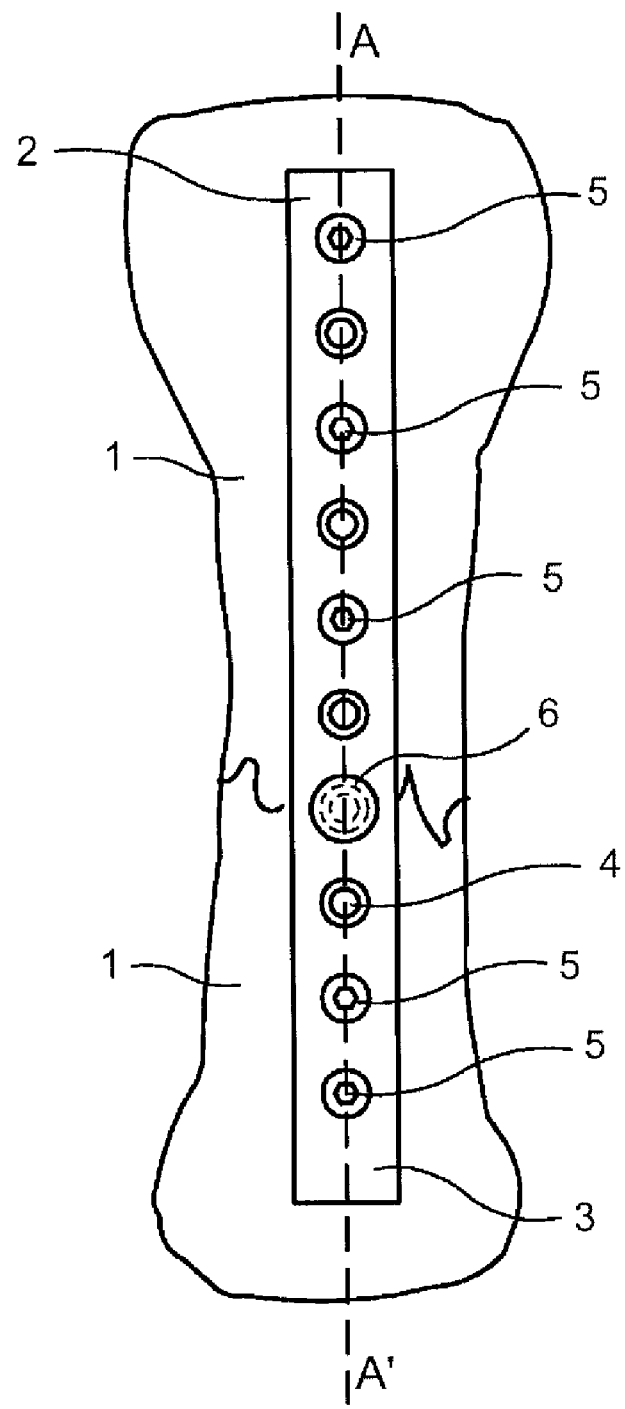

| | | | |
|---|---|---|---|
| 5,779,706 A * | 7/1998 | Tschakaloff | 606/281 |
| 5,964,993 A | 10/1999 | Blubaugh, Jr. et al. | |
| 6,034,296 A * | 3/2000 | Elvin et al. | 623/16.11 |
| 6,214,012 B1 * | 4/2001 | Karpman et al. | 606/93 |
| 6,322,562 B1 | 11/2001 | Wolter | |
| 6,447,448 B1 * | 9/2002 | Ishikawa et al. | 600/300 |
| 6,464,687 B1 * | 10/2002 | Ishikawa et al. | 604/891.1 |
| 6,610,096 B2 | 8/2003 | MacDonald | |
| 6,793,659 B2 | 9/2004 | Putnam | |
| 2002/0151770 A1 * | 10/2002 | Noll et al. | 600/300 |
| 2002/0151978 A1 * | 10/2002 | Zacouto et al. | 623/17.12 |
| 2003/0073999 A1 | 4/2003 | Putnam | |
| 2004/0023623 A1 * | 2/2004 | Stauch et al. | 455/115.1 |
| 2004/0204647 A1 * | 10/2004 | Grupp et al. | 600/431 |
| 2005/0137707 A1 * | 6/2005 | Malek | 623/17.12 |
| 2007/0233065 A1 * | 10/2007 | Donofrio et al. | 606/61 |

FOREIGN PATENT DOCUMENTS

| | | |
|---|---|---|
| DE | 19858889 A1 | 6/2000 |
| DE | 10048375 A1 | 5/2002 |
| DE | 10055519 A1 | 6/2002 |
| DE | 10137011 A1 | 2/2003 |
| EP | 0559870 B1 | 8/1996 |
| WO | 0119239 A1 | 3/2001 |
| WO | 0149173 A1 | 7/2001 |
| WO | 03092514 A1 | 11/2003 |

* cited by examiner

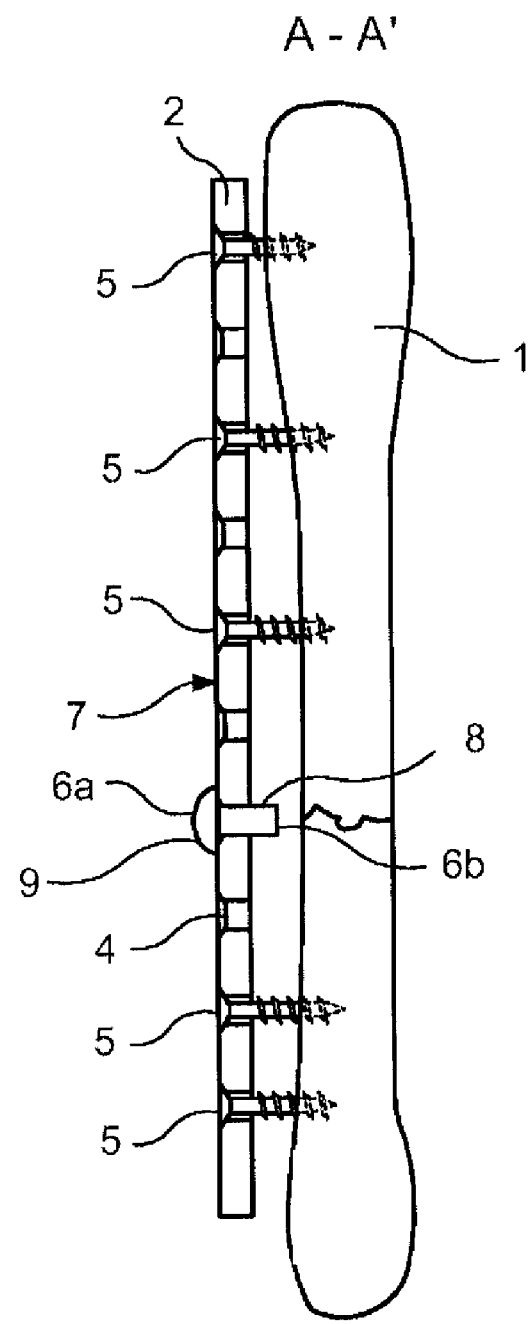
F I G. 2

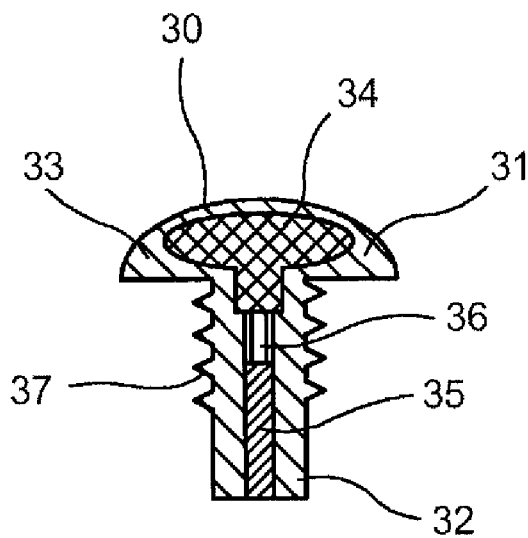
F I G. 3
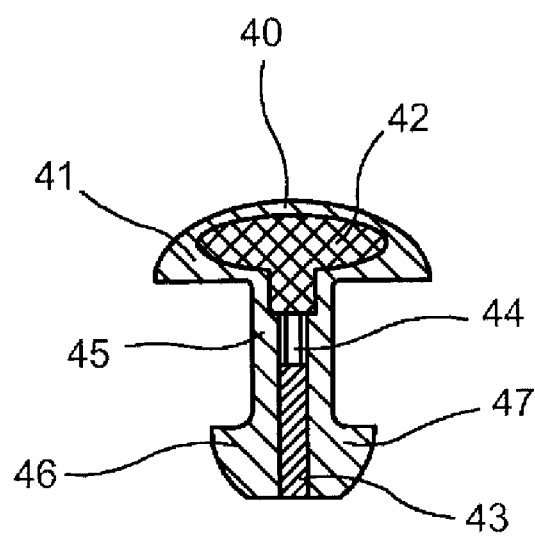
F I G. 4

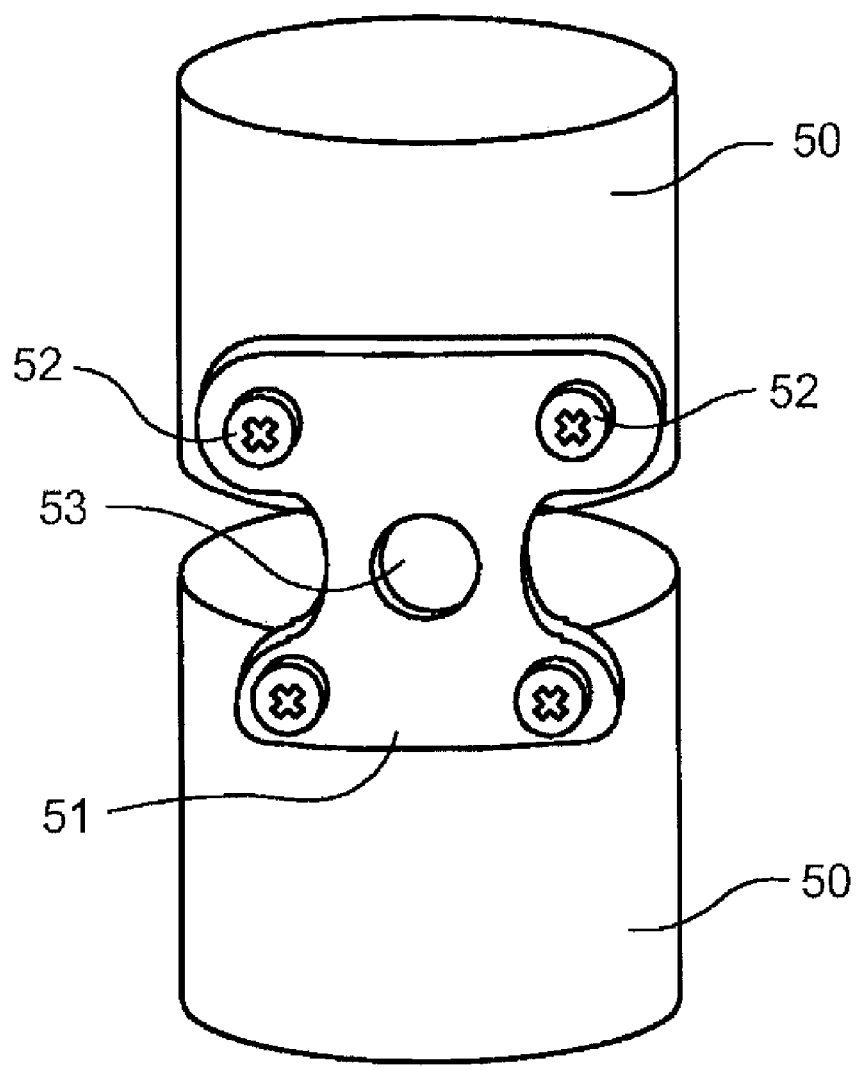
F I G. 5

COMPONENT AND METHOD FOR ASSEMBLING AN IMPLANT ARRANGEMENT

Implants are used both for humans and animals in order to support functions of the bone skeleton or even to replace parts of the skeleton. The implants, which support functions of the skeleton and which can therefore also be described as supporting implants, include plates, splints or angular-stable systems made from a solid material such as, for example, high-quality steel or titanium which are secured to skeleton bones in order to take over their supporting function. Such supporting implants are used, for example, in conjunction with bone fractures in order to fixate bone parts relative to one another during the healing process. In this case, implants are secured to the bones with the help of screws, for example. For the purpose of joining bone surfaces together involving bone fractures or in plastic surgery, special implants are used such as, for example, plates or angular-stable systems. For the fixation of the bones, the bone fragments are joined to the plates by means of screws or bolts in particular. In order to allow an adaptation of the osteosynthesis to the individual patient situation, the plates are provided with several openings for accommodating the screws or bolts.

The healing, for example the healing of a bone fracture, is a biological process whose process depends on numerous biological but also bio-mechanical ambient factors. There are proposals for supporting the healing by means of systemic or local application of stimulating substances. The release of corresponding substances in the timing sequence and the effects on relevant bio-physical and/or bio-chemical parameters at the location of interest can be only insufficiently assessed at the present time. Independent of effected/non-effected support, the progress of the healing process is presently assessed on the basis of methods which have serious disadvantages.

The evaluation of X-ray photos is the standard method for the documentation of the healing progress where bone fracture healing is concerned. However, this method involves a radiation load for the patient and is therefore an invasive method where, in addition, an objectified documentation of the healing process is only restrictively possible. The decision as to when the healing process is completed, to the extent that a temporarily applied implant can be removed again for example, is therefore essentially determined by the experience of the surgeon. Methods for the assessment of the healing progress on the basis of computed tomography are also invasive methods because of the radiation load. For a lying implant the evaluation is normally difficult, but is also intensive with regard to time and resources and involves very high costs, and therefore a routine application is not possible. The same applies for MR-based methods that are time-intensive, not always applicable for a lying implant or have a limited validity of statement, are cost-intensive and cannot be applied in large numbers. For special methods for the stabilisation of fractures, for example with so-called "fixateur externe", non-invasive methods are applicable which document in a non-contact manner the change in the relative movement of the bone fragments with the help of optical measurements (G. N. Duda, B. Bartmeyer, S. Sporrer, W. R. Taylor, M. Raschke, N. D. Haas; "Does partial weight bearing unload a healing bone in external ring fixation?"; Langbecks Arch Surg., October 2003, 388(5), 298-304) and can thus illustrate the course of the healing. For stabilising methods where implants, for example, plates, angular-stable "fixateur interne" lie underneath the skin and the securing elements are not accessible for an optical measurement, the non-contact method as described beforehand is not applicable.

U.S. Pat. No. 6,034,296 describes a sensor system for fixation to an implant. The sensor system is equipped with a pressure-measuring system in order to measure the mechanical stresses and strains occurring in the implant during everyday usage. For this purpose, the sensor system is secured to the implant with the help of screws or by means of welded joints. In addition, the sensor system comprises a telemetry unit for the purpose of transmitting the measured values to an external receiver.

DE 198 58 889 A1 discloses an implant for the fixation of bones. As an embodiment form, it is proposed to arrange on the implant a sensor for the detection of forces acting on the implant as well as a telemetry unit for the transmission of the measuring results to an external unit.

The task assignment of the invention is to state and present an improved component that can be used in combination with an implant, so that the detection of medically relevant measurement variables is facilitated. In addition, the assembly of the component is to be uncomplicated as far as possible.

This task assignment is solved by means of a basic component and a supporting implant, as will be described in greater detail hereinafter.

The invention comprises the line of thought of presenting a component for arrangement on an implant whereby the component has the following features: a basic component, at least one sensor device arranged in the basic component for detecting a measurement variable and for producing measuring data for the detected measurement variable, a telemetry device arranged in the basic component for transmitting and/or receiving data and a data transmission connection between the at least one sensor device and the telemetry device for the transmission of data between the at least one sensor device and the telemetry device, whereby the data comprise the measuring data and whereby, at the basic component, assembly means for the detachable mounting of the basic component in an implant recess of an implant are formed.

In this way, a component is made available which can be mounted in a uncomplicated manner on the implant to be implanted. The assembly of the basic component with the at least one sensor device and the telemetry device at the implant has the advantage that, in this way and in spatial vicinity to the implant which itself is placed in the body of the living being at a location at which a process to be observed, for example a healing process, is in progress, measuring data can be recorded with the help of the sensor device and these measuring data, following a transmission from the sensor device to the telemetry device, can be called off from outside of the body of the living being from the telemetry device by means of a data read-out ("passive performance", for example by means of a transponder technique) or sent from the telemetry device ("active performance") and can be evaluated in an evaluation device. The integration of sensor device and telemetry device at the implant, made possible with the help of the proposed constructive design of the component, supports a measuring value recording spatially and as close as possible to that particular location where changes in the progress of the healing process can be observed. After mounting the component in the implant, this design of the component therefore makes possible the monitoring of fracture healing processes, for example. Sensor devices which are known as such to the expert can be arranged in this way with a minor effort to an implant. The measurement performed with the help of the sensor device concerns, for example, a pH-value-measurement, an oxygen partial pressure measurement, a pressure measurement (liquid pressure), an acceleration measurement and/or a protein concentration measurement.

A purposeful embodiment of the invention can envisage that the component is arranged in an implant recess. In this way, the solid localisation of the component at the implant is facilitated.

One possibility for mounting the basic component onto the implant with a minor effort is created by a preferred embodiment of the invention in such a way that the assembly devices comprise an assembly section for at least partial insertion into the implant recess. The at least partial insertion of the assembly section of the basic component ensures a stable holding of the basic component at the implant.

It can be envisaged with one embodiment of the invention that, in the zone of the assembly section, a threaded section form screwing in the basic component into the implant recess is formed. The screw type fixation of the component made possible with the help of the threaded section allows a reliable securing and loosening of the component at the implant.

With an advantageous embodiment form of the invention the component is prevented from slipping all the way through the implant recess in that the basic component in the longitudinal section has an essentially T-shaped cross-section with a head part and a base part. The head part which is wider in comparison to the base part prevents the component from making its way too far into the implant recess.

With a further development of the invention it can be envisaged that the at least one sensor device is arranged in the zone of an end section of the basic component, and the telemetry device is arranged in the zone of an oppositely located end section of the basic component. In this way, the at least one sensor device can be arranged as near as possible to a location to be examined at which the measurement variable is to be detected. Then again, the telemetry device with this embodiment can be possibly arranged in such a way that a disturbance-free reception/transmission of the data is ensured. This is particularly supported in a further embodiment form of the invention in such a way that the telemetry device is arranged essentially in the head part of the basic component. When arranging the component at the implant, the head part is not inserted into the implant recess so that it is exposed to the greatest possible extent. This facilitates the non-disturbed transmission/reception of data.

In a purposeful embodiment of the invention it is envisaged that a receiving chamber for accommodating an active ingredient is formed at the basic component, whereby the receiving chamber is connected to an opening for discharging the active ingredient to the outside. A possibility is created in this way for implanting a medical active ingredient together with the implant, whereby the active ingredient is located in the receiving chamber.

A discharging device is envisaged with an advantageous embodiment of the invention for the purpose of a controlled discharge of the active ingredient from the receiving chamber through the opening within the framework of an active ingredient application. The discharging device can comprise a pump device for pumping a volume of the active ingredient from the receiving chamber through the opening. In addition, the preferred further development of the invention envisages that the discharging device comprises an opening mechanism for opening/closing the opening. In this way, various embodiments of a component are formed where said component can be used to the effect that not only measuring data can be detected and transmitted with the help of the telemetry device but that also an active ingredient can be provided at a location near the implant. Micro-mechanisms for forming the discharging device, a pump and/or the opening mechanism are known as such to the expert, for example from the field of micro-system technology in medical or non-medical applications.

With one embodiment form of the invention it is purposefully envisaged that the discharging device is connected to the telemetry device by way of a data transmission connection for the purpose of transmitting data. In this way, the possibility is created for transmitting electronic data to the discharging device from the outside and/or for receiving electronic data from the discharging device by way of the telemetry device. In this way the discharge of the active ingredient from outside of the body, in which the implant with the component is used, can be controlled.

In addition, a further development of the invention can envisage a control unit which is connected to the at least one sensor device and the discharging device in order to control in common the detection of the measuring data with the help of the at least one sensor device and the discharge of the active ingredient with the help of the discharging device. A common control in this context means a control system that is essentially inter-coordinated, so that the detection/recording of measuring data and the discharge of the active ingredient can be correlated with one another from timing aspects, for example.

The described component with the at least one sensor device, the telemetry device and the mounting devices at the basic component can be arranged both in an implant recess of a supporting implant, particularly a plate, a "nail" (marrow nail) or a splint made from a material with a high degree of rigidity, as well as in an implant recess of a substitute implant, particularly a synthetic hip, knee or shoulder joint. In this case the assembly effort is minimised if the implant recess is a usable assembly recess, during the implanting process, for accommodating implant securing devices. Such assembly recesses are normally envisaged in implants in order to secure the implant with the help of screws or similar securing devices. The arrangement of the component in such an assembly receptacle, which is redundant for the securing of the implant, avoids additional mechanical working on the implant in order to enable the arrangement of the component. An uncomplicated but, with regard to the mechanical fixation, secure arrangement of the component is ensured with an embodiment of the invention in such a way that the implant recess has an internal thread section into which the component is screwed.

Figure 6:
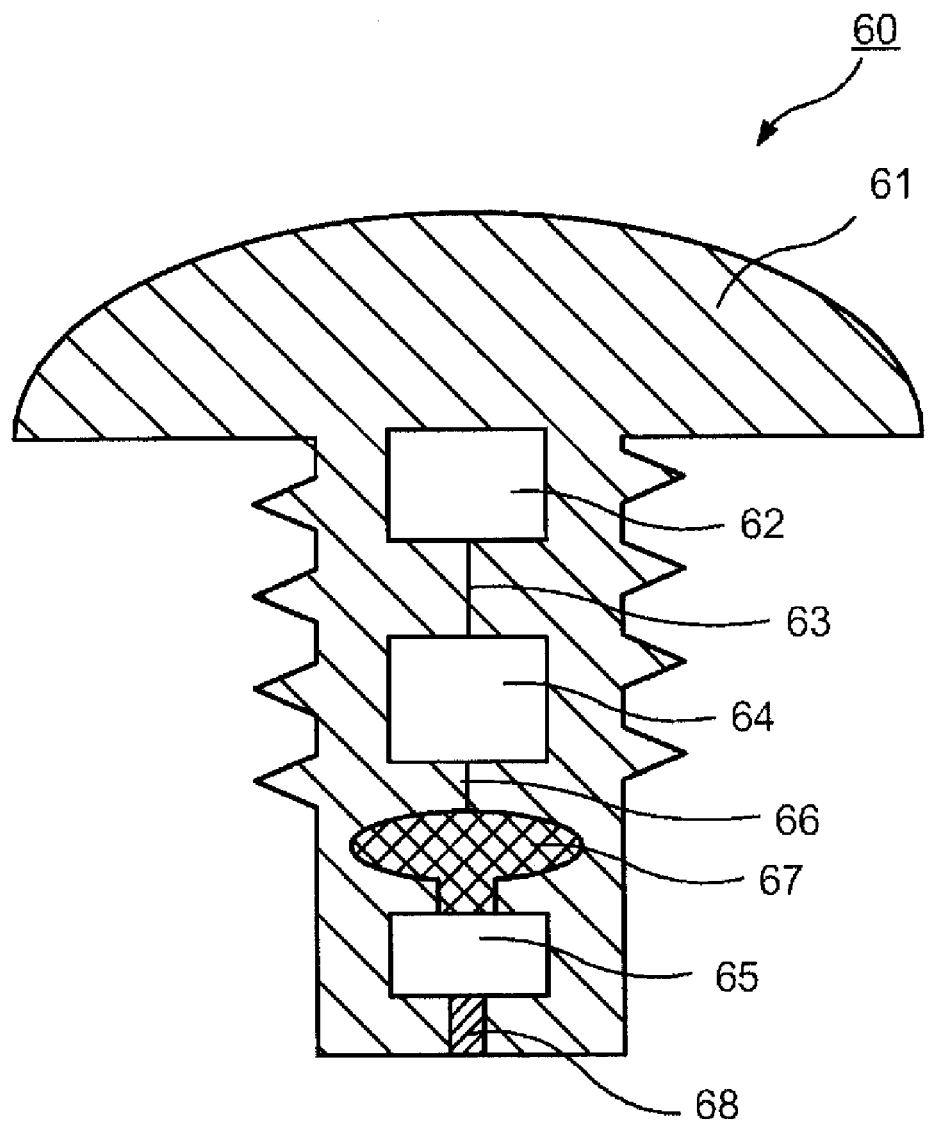

The invention is explained as follows in greater detail on the basis of embodiment examples with reference to a drawing. The Figures show the following:

FIG. 1: an arrangement with a bone and an implant secured to it;

FIG. 2: a cross-sectional illustration of the arrangement according to FIG. 1 along a line AA';

FIG. 3: a component for mounting on an implant with a sensor device and a telemetry device in the cross-section;

FIG. 4: a further component for mounting on an implant with a sensor device and a telemetry device in the cross-section;

FIG. 5: a schematic illustration of a vertebral body with an implant secured to it; and FIG. 6: another component for mounting on an implant with a sensor device and a telemetry device in the cross-section.

FIG. 1 shows a bone fragment 1 with an implant 2 secured to it, involving a splint 3 with several openings 4 that are executed as full-through bores. Screws 5 are arranged in a part of the openings 4 and these screws serve the purpose of securing the implant 2 to the bone fragment 1. For this purpose the screws 5 are screwed into the bone fragment 1, to be seen more distinctly in FIG. 2 which shows a cross-section through the bone fragment 1 and the implant 2 according to FIG. 1 along the line AA'.

A part of the openings 4 in the splint 3 that are usable for mounting the implant 2 are not used for fixation by means of the screws 5. A component 6 is inserted into one of these non-used openings. In this case, the component 6 can be plugged or screwed into the splint 3. A head part 6*a* of the component 6 is arranged on a outer surface 7 of the splint 3. A base part 6*b* of the component 6 extending from the head part 6*a* extends all the way through the opening in the splint 3, so that an end section 8 of the base part 6*b* is arranged oppositely located to the bone fragment 1. An oppositely located end section 9 in the zone of the head part 6*a* is at a distance from the bone fragment 1 and is placed essentially free on the outer surface 7 of the splint 3.

Embodiment forms of the component 6 are shown in detail in the FIGS. 3 and 4. With the embodiment form of a component 30 according to FIG. 3, the component 30 in the illustrated longitudinal section has a mushroom-shaped cross-section with a head part 31 and a base part 32. The component 30 comprises a base component 33 in which a telemetry device 34 and a sensor device 35 are arranged. The sensor device 35 and the telemetry device 34 are connected up together by way of a data transmission device 36. With the help of the sensor device 35, measuring data can be detected for one or several physical measurement variables, for example pH-value, oxygen partial pressure, pressure, expansion, acceleration, protein concentration and/or strain. Sensors known as such and which are suitable for the integration into the base component 33 can be selected by the expert according to the measuring application to the performed. With the help of the sensor device 35 and the telemetry device 34, a telemetric measuring sensor unit is established. The sensor device 35 is, for example, a measuring chip, a thermistor, an ASIC or similar.

The telemetric measuring sensor unit can be formed as an active module having its own power supply, a battery and/or a rechargeable battery which provides the required power at least intermittently. It can also be executed as a passive module where the required power for the sensor device 35 and the telemetry device 34 is taken from the outside as required by way of a cable-free connection.

The measuring data generated in the sensor device 35 for the measurement variable(s) are transmitted from the sensor device 35 by way of the data transmission connection 36 to the telemetry device 34. The telemetry device 34 has suitable transmission/reception means in order to transmit the measuring data, upon enquiry, cable-free to an evaluator (not shown). The data transmission can be performed with the help of read-out of data, for which purpose an external reading system (not shown) is used. The purpose of the reading system is to read the data from the sensor device 35 directly or by way of the telemetry device 34 on cable-free, telemetric routing and, as required, to supply these to a socalled "data logger" or an evaluation unit. It can be envisaged that the reading system is capable of providing a power supply for the telemetric measuring sensor unit. If the telemetric measuring sensor unit has its own power supply, for example in the form of a battery or a rechargeable battery, this can be charged with the help of the reading system by way of a cable-free connection.

The electronic components of the system comprise a signal conditioning chip (e.g., ASIC) with AD-transformer and filtering, a digital interface for computer hook-up, a transponder-IC with integrated processor, a storage medium, a real-time clock, an aerial coil and, as required, a power source with power management. The signal conditioning chip/ASIC enables an electronic correction of the individual sensor errors and subsequently allows a high precision measurement of the vital parameters.

The casing for the telemetry unit consists of a bio-compatible polymer material, with and without coating. The form and the technical execution depends on the location of deployment and/or the application. A sleep-mode can be activated within the framework of the power management for the purpose of reducing the power consumption or in the event of a non-existent power supply.

After the arrangement of the component 30 in an implant, for example in the implant 2 as shown in FIG. 1, and after the implantation of the implant in the body of a living being, it is possible in this way to detect measuring data and to transmit these to an evaluator outside of the body of the living being. The transmission of such measuring data, in conjunction with sensors in the body of a living being, is known as such and is therefore not explained in further detail here.

According to FIG. 3, a threaded section 37 is envisaged at the base part 32 and this threaded section serves the purpose of screwing in the component 30 into the implant recess during the assembly at the implant.

FIG. 4 shows a cross-section of a further component 40 which can be used, for example, as an embodiment form for the component 6 in the arrangement according to FIG. 1. A telemetry device 42 as well as a sensor device 43 are envisaged in the basic component 41 of the component 40. Again, a data transmission connection 44 is envisaged for the transmission of measuring data, generated with the help of the sensor device 43, to the telemetry device 42. In contrast with the embodiment form according to the FIG. 3, the component 40 does not have a threaded section in the zone of the base part 45. A broadened foot part 46 is rather envisaged. If, during the arrangement in a implant recess with the foot part 46, the component 40 is first inserted into the implant recess, then the projecting lateral sections 47 of the foot part 46 press against the wall of the implant recess. As a result, a clamping effect for the fixation of the component 40 at the implant is effected. It can be envisaged in this case that the basic component 41 is formed from a material that is yielding in a certain scope so that the projecting lateral sections 47 can be partly pressed inwards when inserting into the implant recess.

Depending on the application cases the expert can select between various materials for the basic components 41 and 33, respectively. Whereas for the embodiment form of the component 30 a rather solid material is to be used, for example a metal in order to form the threaded section 37, a material can be selected for the embodiment form of the component 40 which is elastically or non-elastically workable in a certain scope, for example a plastic material. If the component 40 is partially inserted all the way through an implant recess executed as a break-through, the foot part prevents the component 40 from slipping out.

FIG. 5 shows a vertebral body 50, to which an implant 51 is secured with screws 52. A opening 53 in the implant 51 is non-used, so that a component can be arranged in this opening 53, as described for example with reference to the FIGS. 3 and 4.

FIG. 6 shows another component 60 in cross-section illustration which can be used in particular as an embodiment form for the component 6 in the arrangement according to FIG. 1. An application unit 62 is integrated in an enclosure 61. With the help of a sensor unit (not shown) the application unit 62 receives detected measuring signals by way of a cable-free or cable connection for electronic data transmission. The application unit 62 is connected to a control unit 64 by way of a signal line 63. In the control unit 64, typical characteristic curves in the form of electronic data are stored in a storage unit for the measuring signals to be detected with the help of the sensor unit. The typical characteristic curves can be replaced from the outside by changed characteristic curves by way of a telemetry connection of the sensor unit. In the control unit 64, and for activating a pump device 65 which is connected to the control unit 64 by way of a control line 66, control signals are generated on the basis of an actual value/required value comparison of the detected measuring signals with the stored data for the typical characteristic curves. In dependence of the control signals and with the help of the pump device 65, an active ingredient is discharged from an active ingredient reservoir 67 by way of an opening 68 which can be shut off as required. The active ingredient is a chemical compound of any random type that is discharged to the surroundings of the other component 60 for the purpose of achieving a medical effect, for example for the purpose of influencing a healing process. Based on the active ingredient discharge, a change of the detected measuring signals at the sensor unit can be expected. The changed measuring signals at the sensor unit are again compared in the control unit 64 with required values following transmission to the application unit 62, so that a type of control loop for the ingredient discharge is established. For the purpose of implementation of the other component 60 according to FIG. 6, the expert can select microprocessor technology as well as micro-system technique, for example micro-pump technique, which is known in various forms.

The active ingredient discharge can also be effected passively, for example by means of a biodegradable (matrix) system or the release by means of diffusion from a matrix.

The features of the invention as disclosed in this description, in the claims and in the drawing can be of significance both individually as well as in random combination for the realisation of the invention in its various embodiment forms.

The invention claimed is:

1. A component for an arrangement at an implant, comprising:
    a basic component, including:
        at least one sensor device detecting a measurement variable and generating measuring data for the detected measurement variable;
        a telemetry device at least one of transmitting and receiving data;
        a data transmission connection arranged in the basic component between the at least one sensor device and the telemetry device for the transmission of data therebetween, the data including the measuring data;
        an assembly arrangement detachably mounting the basic component in an implant recess of the implant; and
        a receiving chamber located within the basic component and configured to accommodate an active ingredient therein, the receiving chamber extending to an opening at a first end section of the basic component for discharging the active ingredient therefrom,
    wherein the basic component is configured to be insertable through an implant recess of an implant positioned over a target portion of a bone so that the opening is seated over an outer periphery of the target portion of the bone.

2. The component according to claim 1, wherein the assembly arrangement includes an assembly section configured to be at least partially inserted into the implant recess.

3. The component according to claim 2, further comprising, in the zone of the assembly section, a threaded section configured to be screwed into the implant recess.

4. The component according to claim 1, wherein the basic component has in a longitudinal section an essentially T-shaped cross-section with a head part and a base part.

5. The component according to claim 4, wherein the at least one sensor device is arranged in the zone of the first end section of the basic component and the telemetry device is arranged in a zone of an oppositely located second end section of the basic component.

6. The component according to claim 4, wherein the telemetry device is arranged in the head part of the basic component.

7. The component according to claim 1, further comprising:
    a discharge device configured to control discharging of the active ingredient from the receiving chamber through the opening.

8. The component according to claim 7, wherein the discharge device includes a pump device pumping a volume of the active ingredient from the receiving chamber through the opening.

9. The component according to claim 8, wherein the discharge device includes an opening mechanism opening/closing the opening.

10. The component according to claim 9, wherein the discharge device is connected using a further data transmission connection to the telemetry device for the transmission of data.

11. The component according to claim 10, further comprising:
    a control unit connected to the at least one sensor device and the discharge device to control (a) the detection of the measuring data using the at least one sensor device and (b) the discharge of the active ingredient using the discharge device.

12. The component according to claim 1, further comprising:
    a supporting implant.

13. The component according to claim 12, wherein the implant recess is a usable assembly recess configured to accommodate an implant fixation device.

14. The component according to claim 13, wherein the implant recess has an internal thread section.

15. The component according to claim 13, wherein the supporting implant is one of a synthetic hip, a knee and a shoulder joint plate.

16. The component according to claim 14, wherein the supporting implant is one of a plate and a splint formed of a material with a high degree of rigidity.

* * * * *

UNITED STATES PATENT AND TRADEMARK OFFICE
CERTIFICATE OF CORRECTION

PATENT NO. : 8,343,153 B2  
APPLICATION NO. : 10/597842  
DATED : January 1, 2013  
INVENTOR(S) : Duda et al.

Page 1 of 1

It is certified that error appears in the above-identified patent and that said Letters Patent is hereby corrected as shown below:

Col. 8, lines 52-54, Claim 15 should read as follows:

-- 15. The component according to claim 12, wherein the supporting implant is one of a synthetic hip, a knee and a shoulder joint plate. --

Col. 8, lines 55-57, Claim 16 should read as follows:

-- 16. The component according to claim 12, wherein the supporting implant is one of a plate and a splint formed of a material with a high degree of rigidity. --

Signed and Sealed this  
Nineteenth Day of February, 2013

Teresa Stanek Rea  
*Acting Director of the United States Patent and Trademark Office*